(12) United States Patent
Tanaka

(10) Patent No.: US 6,646,254 B2
(45) Date of Patent: Nov. 11, 2003

(54) LIQUID CHROMATOGRAPH MASS SPECTROMETER

(75) Inventor: Yasufumi Tanaka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 256 days.

This patent is subject to a terminal disclaimer.

(21) Appl. No.: 09/845,287

(22) Filed: May 1, 2001

(65) Prior Publication Data

US 2001/0050337 A1 Dec. 13, 2001

(30) Foreign Application Priority Data

May 31, 2000 (JP) ........................................ 2000-162253

(51) Int. Cl.[7] ................................................ H01J 49/42
(52) U.S. Cl. ........................ 250/288; 250/281; 250/292
(58) Field of Search ................................ 250/288, 281, 250/292, 294

(56) References Cited

U.S. PATENT DOCUMENTS 6,462,338 B1 * 10/2002 Inatsugu et al. ............ 250/292

6,472,661 B1 * 10/2002 Tanaka et al. .............. 250/281

* cited by examiner

Primary Examiner—John R. Lee
Assistant Examiner—Phillip A Johnston
(74) Attorney, Agent, or Firm—Kanesaka & Takeuchi

(57) ABSTRACT

A liquid chromatograph mass spectrometer includes a solvent removing tube, a first ion lens and a second ion lens. Voltages applied to the solvent removing tube, and the first and second ion lenses corresponding to each mass number of a standard sample are studied in advance so that efficiencies of passing ions become best. A voltage scanning pattern is made based on the impressed voltages, and stored in a memory portion. When a scanning measurement is carried out, a control portion controls a current voltage source and a high frequency voltage source according to the voltage scanning pattern, synchronizing with the scanning of the impressed voltage to the quadrupole filter. As a result of the control, an objective ion which is generated by being atomized from a nozzle may effectively pass through the entrance of a quadrupole filter.

6 Claims, 4 Drawing Sheets

LIQUID CHROMATOGRAPH MASS SPECTROMETER

BACKGROUND OF THE INVENTION AND RELATED ART STATEMENT

The present invention relates to a liquid chromatograph mass spectrometer (hereinafter referred to as LC/MS).

In the LC/MS, an interface is used in order to ionize a liquid sample separated and eluted from a column of a liquid chromatograph (LC) section corresponding to a retention time, and introduce the ion into a mass spectrometer (MS) section. The interface includes an ionizing device for generating ions while atomizing gas ions, by utilizing means for heating, a high-speed air flow, a high electric field or the like. The interface also includes an ion lens which suitably focus ions, and accelerate ions to be sent to subsequent sections, if necessary.

In order to improve a sensitivity for analyzing by the LC/MS, it is important for the ionizing device as described above to ionize the liquid sample effectively, namely to improve the efficiency of generating the ions. It is also important to introduce ions into a mass separator effectively, for example quadrupole filter, namely to improve the passing efficiency of ions into the mass separator. To achieve the improvement, it is necessary that conditions, such as a temperature of each part of the interface and impressed voltage, are set appropriately.

In the conventional LC/MS, when a standard sample including a defined content is introduced into a mass separator through the interface, the applied voltages to the respective parts, such as the ion lens, are adjusted so that the number of ions which reach an ion detector may be maximum, concretely a peak of a mass spectrum corresponding to the defined content becomes highest. In fact, however, the conditions where ions pass through most effectively also depend on the number of ions. Therefore, in case that a scanning measurement is carried out in a designated mass range, the impressed voltages of the parts, such as the ion lens, is not always most suitable for passing of the ions. This is one of the reasons that the sensitivity and an accuracy of detection become worse.

The present invention has been made in order to solve the foregoing problems, and an object of the invention is to provide a liquid chromatograph mass spectrometer in which the sensitivity and accuracy of the detection are improved by introducing object ion into the mass separator section effectively.

Further objects and advantages of the invention will be apparent from the following description of the invention.

SUMMARY OF THE INVENTION

To solve the aforementioned problems, the present invention provides a liquid chromatograph mass spectrometer having an interface, which includes an ionization chamber, in which a liquid sample supplied from a liquid chromatograph portion is atomized and ionized at about an atmospheric pressure, and a generated ion in the ionization chamber is introduced into a mass separator under high vacuum condition through a first intermediate chamber and a second intermediate chamber.

The liquid chromatograph mass spectrometer includes a solvent removing tube disposed in the interface for carrying a droplet including the ion from the ionization chamber to the first intermediate chamber; a first ion lens disposed in the first intermediate chamber, and having a plural of board electrodes arranged along an ion optical axis c; a second ion lens disposed in the second intermediate chamber, and having 2n rod electrodes, n being an integer and at least two, which is arranged along the ion optical axis c; first voltage generation means for applying direct current to the solvent removing tube; a second voltage generation means for applying high frequency voltage superposed on the direct current voltage to the board electrodes; a third voltage generation means for applying high frequency voltage superposed on the direct current voltage into the rod electrodes; a memory means for storing voltage data for the solvent removing tube, the first ion lens and the second ion lens corresponding to a mass number so that an efficiency of passing of the ions becomes best; and control means for controlling the first, the second and the third voltage generation means so that the voltages based on the voltage data which are stored by the memory means can be applied to the solvent removing tube, the first ion lens and the second ion lens when an appropriate voltage corresponding to a mass number of the sample is applied to the mass separator.

In the liquid chromatograph mass spectrometer of the invention, for example, the applied voltages to the solvent removing tube, the first ion lens and the second ion lens are respectively studied in advance with respect to each mass number by analyzing one or a plurality of standard samples including a plurality of different components which have different mass number so that an efficiency of passing of ions becomes best. Based on the results of the study, voltage scanning patterns for determining the best or almost the best applied over a whole range of the mass numbers which can be analyzed, are made and stored in a memory portion.

When a scanning measurement is carried out, the voltage is applied or scanned to the mass separator so that the ions having the specific mass number, which are the subject of analyzing, may only pass through in sequence. Control means changes the applied voltage to the solvent removing tube, the first ion lens and the second ion lens by controlling the first, the second and the third voltage generating means according to the voltage scanning patterns stored in the memory section, synchronizing with the scanning of the applied voltage with respect to the mass separator. The ions in the best or almost the best condition pass through the path from the entrance of the solvent removing tube to the mass separator by the control means. Accordingly, more ions are introduced into the mass separator and the number of the ions reaching to the ion detector increases.

Incidentally, the voltage scanning patterns as described above have almost fixed shapes of straight lines or curve lines. It is desirable that pattern making means, which makes the voltage scanning pattern by suitably complementing between the plural scattered data given by measuring the standard sample, according to a designated algorithm, is provided. In the pattern making means, although there are few points of the mass numbers measured in advance, almost the best voltage scanning pattern can be made. Therefore, more appropriate voltage can be applied to the solvent removing tube, the first ion lens and the second ion lens.

According to the liquid chromatograph mass spectrometer of the present invention, since the efficiency of introducing the objective ion into the mass separator is improved regardless of the mass number of the ion, the efficiency of the detection of the ions by the ion detector is improved. Accordingly, the accuracy and sensitivity of the analysis by using the mass spectrometer is improved, and a repeatability is also improved.

DETAILED DESCRIPTION OF PREFERRED EMBODIMENTS

Figure 1:
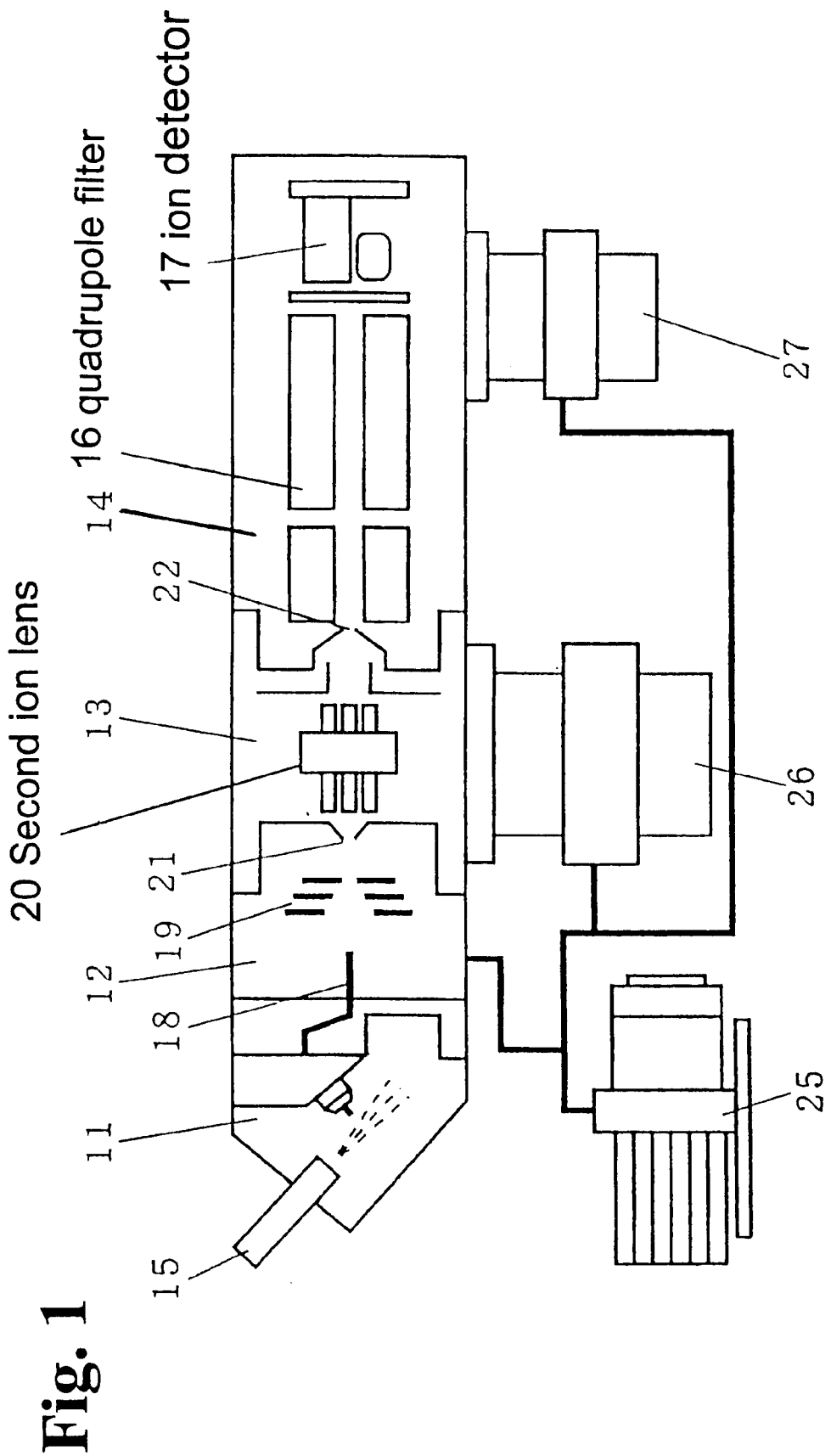
FIG. 1 is a view for schematically explaining an example of the LC/MS of the present invention.

Hereunder, embodiments of an LC/MS of the present invention are explained with reference to the attached drawings. FIG. 1 is a view for schematically explaining an example of the LC/MS of the present invention. This apparatus has an ionization chamber 11 and a mass spectrometry chamber 14. The apparatus also has a first intermediate chamber 12 and a second intermediate chamber 13 which are disposed between the ionization chamber and the mass spectrometry chamber, and separated by a partition wall. The ionization chamber 11 has a nozzle 15 which is connected to an exit of a column for liquid chromatograph which is not shown. The mass spectrometry chamber 14 has a quadrupole filter 16 and an ion detector 17. The first intermediate chamber 12 and the second intermediate chamber 13 have a first ion lens 19 and a second ion lens 20, respectively. A solvent removing tube whose internal diameter is very small is provided between the ionization chamber 11 and the first intermediate chamber 12, and these chambers are connected to each other only through the solvent removing tube 18. A skimmer 21 having a through hole (orifice) with a very small diameter is provided between the first intermediate chamber 12 and the second intermediate chamber 13, and these chambers are connected to each other only through the skimmer 21.

An inside of the ionization chamber 11 has approximately an atmospheric pressure because of gas molecules of the liquid sample provided continuously through the nozzle 15. On the other hand, an inside of the mass spectrometry chamber 14 is exhausted by a turbo-molecular pump (TMP) 27 to become a high vacuum condition, such as a range approximately from $10^{-3}$ to $10^{-4}$ Pa for the mass spectrometry. Since a hole has to be provided for passing the ions from the ionization chamber 11 to the mass spectrometry chamber 14, between which there is a large difference in pressure, the first intermediate chamber 12 and the second intermediate chamber 13 are disposed between the ionization chamber 11 and the mass spectrometry chamber 14, and the vacuum conditions are gradually increased from the ionization chamber 11 toward the mass spectrometry chamber 14. Concretely, an inside of the first intermediate chamber 12 is exhausted by a rotary pump (RP) 25 to approximately $10^2$ Pa, and the second intermediate chamber 13 is exhausted by a turbo-molecular pump (TMP) 26 approximately to a range from $10^{-1}$ to $10^{-2}$ Pa.

The liquid sample is atomized into the ionization chamber 11 through the nozzle 15, and the molecules of the sample are ionized during a vaporizing process of solvent of droplets. Generated ions are sucked with the small droplets which are not ionized, by the solvent removing tube 18 due to the pressure difference between the ionization chamber 11 and the first intermediate chamber 12. The first intermediate chamber 12 has the first ion lens 19 therein, an electric field of which helps ions through the solvent removing tube 18 to be sucked and focus the ions around the orifice of the skimmer 21.

The ions which are introduced into the second intermediate chamber 13 through the orifice of the skimmer 21 are focused by the second ion lens 20 and accelerated to be sent to the mass spectrometry chamber 14 through a pin hole 22. In the mass spectrometry chamber 14, only objective ions having specific mass numbers (mass m/charge z) pass through a space along the longitudinal direction of the center of the quadrupole filter 16 to reach the detector 17, and are detected. Incidentally, the central axis of the path of the ions is called an ion optical axis c.

Figure 2:
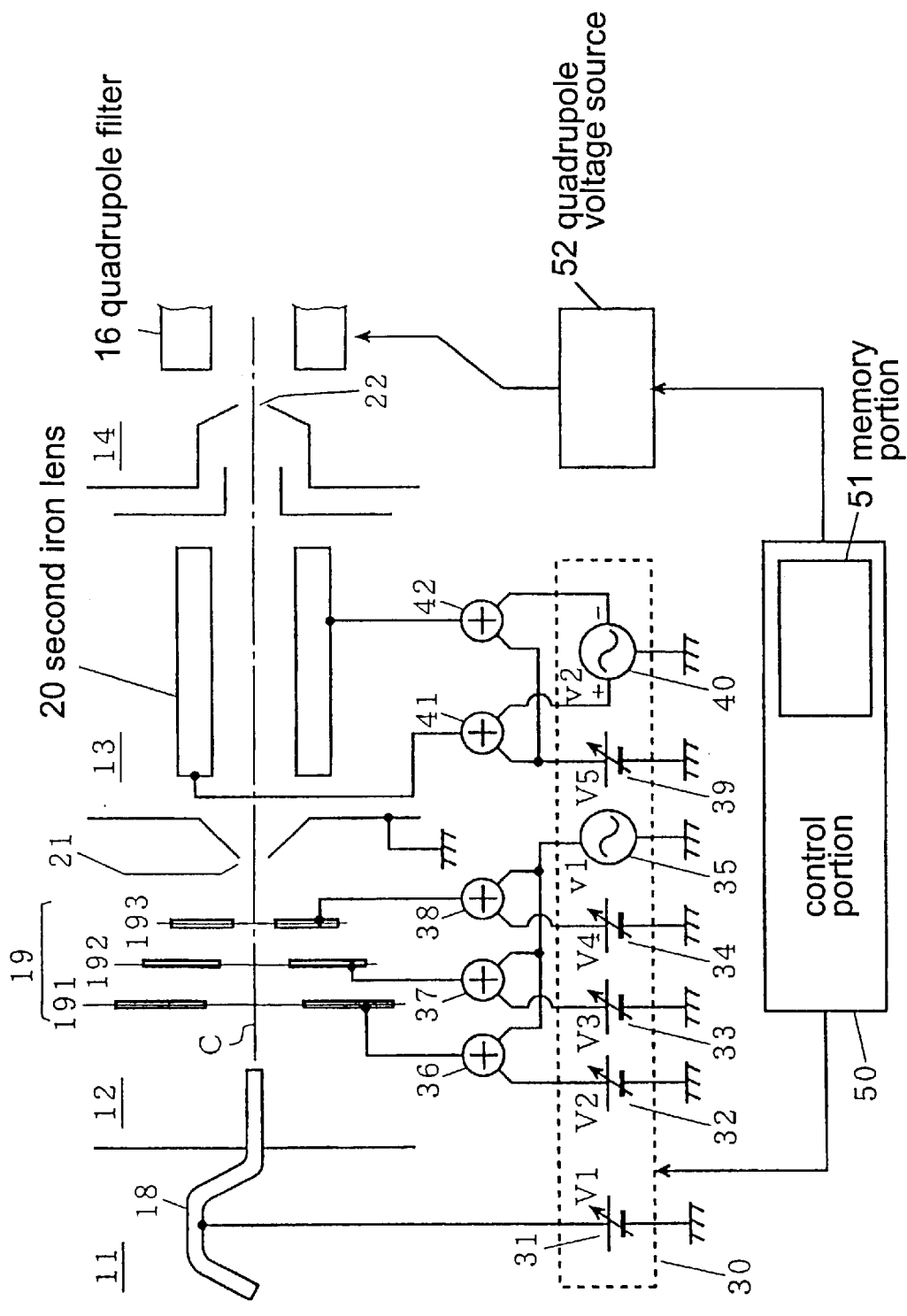
FIG. 2 is a schematic view for explaining a path of ions from a solvent removing tube to an entrance of a mass spectrometry chamber in the example of the LC/MS of the present invention.
Figure 4:
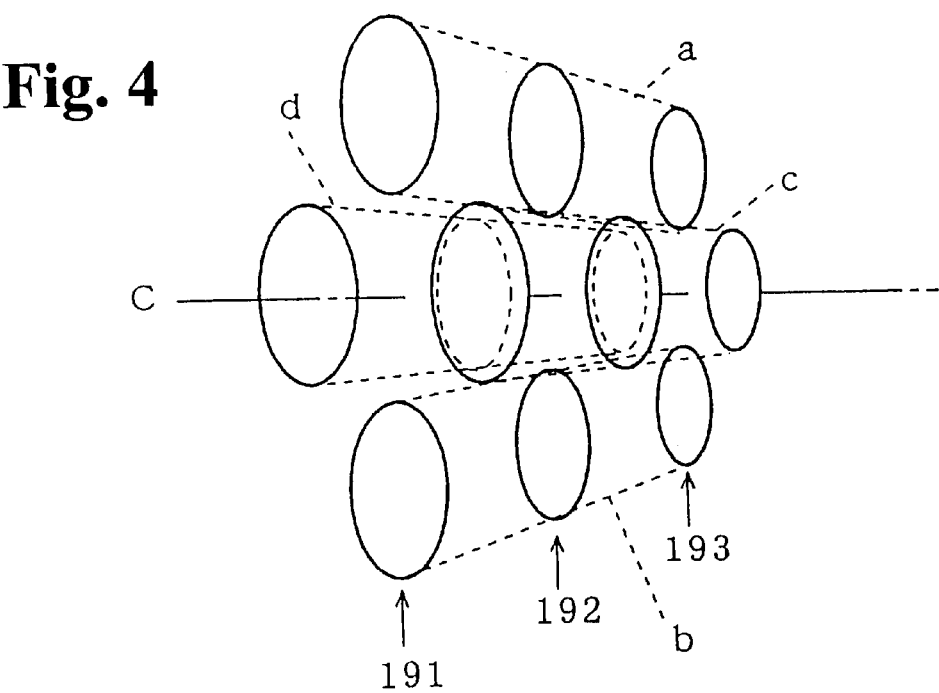
FIG. 4 is an explanatory perspective view of a first ion lens in the example of the LC/MS of the present invention.

FIG. 2 is a schematic view for explaining mainly the path of the ions from the solvent removing tube 18 to an entrance of the mass spectrometry chamber 14 in the example. FIG. 4 is an explanatory perspective view of the first ion lens 19, and FIG. 5 is an explanatory perspective view of the second ion lens 20 in the example of the LC/MS of the present invention.

The solvent removing tube 18 has an opening entrance which is arranged obliquely to a direction of atomizing a droplet from the nozzle 15, and the tube has a bending shape. Accordingly, a relatively large droplet, neutral molecule or the like is prevented from plunging into the solvent removing tube 18.

As shown in FIG. 4, the first lens 19 includes a plurality of disk-shaped metal boards (three boards in FIG. 4), which are arranged at designated intervals along the ion optical axis c to become closer to the ion optical axis c while approaching the skimmer (right direction in FIG. 4) to form virtual rods. Thus, a plural of rods a, b, c and d (four rods in the FIG. 4) is disposed around the ion optical axis C. Accordingly, respective electrode boards contained in the four virtual rods a, b, c and d are included in the planes which are orthogonal to the ion optical axis C, which are shown as 191, 192 and 193 in FIG. 4. That is the ion lens such that an assignee of the present invention presented in detail in Japanese Patent Application No. 11-196856.

Figure 5:
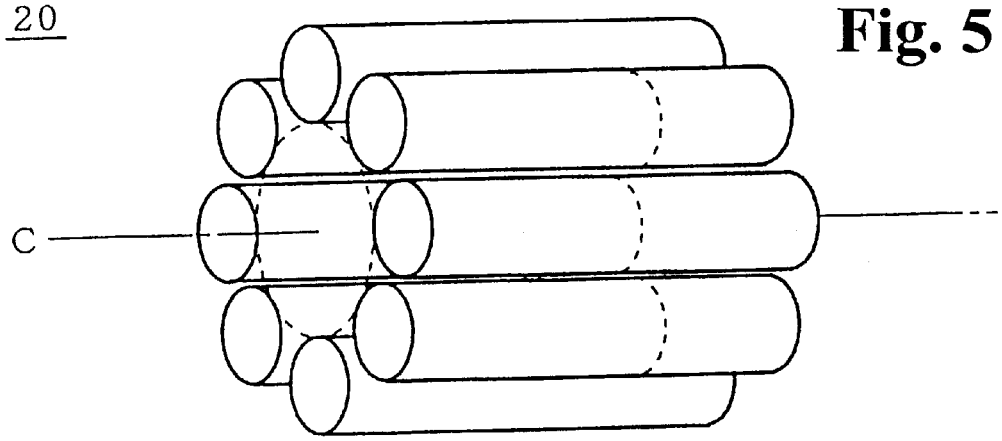
FIG. 5 is an explanatory perspective view of a second ion lens in the example of the LC/MS of the present invention.

On the other hand, as shown in FIG. 5, the second ion lens 20 has more than 4 and even number of rod electrodes (8 rods in the FIG. 5), which are disposed around the ion optical axis C, touching internally a designated circle. The ion lens which is shown in detail by the assignee of the present invention in Japanese Patent Application 11-196856 can be used.

Direct current voltage V1 is applied to the solvent removing tube 18 from a first direct current voltage source 31. High frequency voltage v1 generated at a first high frequency voltage source 35 is superposed on a direct current voltage V2 generated at a second direct current voltage source 32 at a superposing portion 36, and applied to the four board electrodes on the first plane 191 in the ion lens 19. The high frequency voltage v1 is also superposed on direct current voltages V3 and V4 generated at a third direct current voltage source 33 and a fourth direct current voltage source 34 at superposing portions 37 and 38, respectively, and applied to the four board electrodes on the second plane 192 and the third plane 193 in the ion lens 19 in the same way as the first plane.

In the second ion lens 20, the eight rod electrodes are divided into two groups which include four electrodes arranged in every other electrode. A direct current voltage V5 generated at a direct current voltage source 39 is superposed on a second high frequency voltage v2 generated at a second frequency voltage source 40 at a superposing portion 41, and applied to the four rod electrodes of one group. The direct current voltage V5 is superposed on a high frequency voltage whose phase is inverted against the high frequency voltage v2, and applied to the four rod electrodes of the other group. Incidentally, the skimmer 21 becomes a grounded electric potential.

All of the direct current voltage sources 31, 32, 33, 34 and 39, as described above, included in a voltage generation portion 30 and the high frequency voltage sources 35 and 40 are variable voltage sources. The voltages are controlled by a control signal from a control portion 50. For example, the voltage sources as described above have digital-to-analogue converter (D/A converter) and a power amplifier. The control portion 50 having a central processing unit (CPU) generates a digital voltage at the voltage generation portion 30, and a designated voltage may be generated by converting the digital voltage into an analogue voltage by the D/A converter. The control portion 50 has a memory portion 51 which stores the control signal for controlling the voltage sources, that is data required to generate the digital voltage as described above. A quadrupole voltage source 52 is provided in order to apply the voltage, in which the high frequency voltage is superposed on the direct current voltage, to the quadrupole filter 16 in the mass spectrometry chamber 14. The quadrupole voltage source 52 is also controlled by the control portion 50.

A characteristic action of the LC/MS of the example is explained. In the LC/MS, before an unknown sample is measured, a pre-measurement is carried out by using a standard sample including a plurality of different components which have different mass numbers, beforehand. In the pre-measurement, the applied voltages to the solvent removing tube 18, the first ion lens 19 and the second ion lens 20 are adjusted so that a mass spectrum peak corresponding to each mass number may be highest, and the voltages corresponding to the mass numbers are obtained, respectively. Since the mass numbers obtained by the measurement are scattered, the control portion 50 makes a voltage scanning pattern for a designated mass number range based on the relation between the mass numbers and the voltages.

Figure 3A:
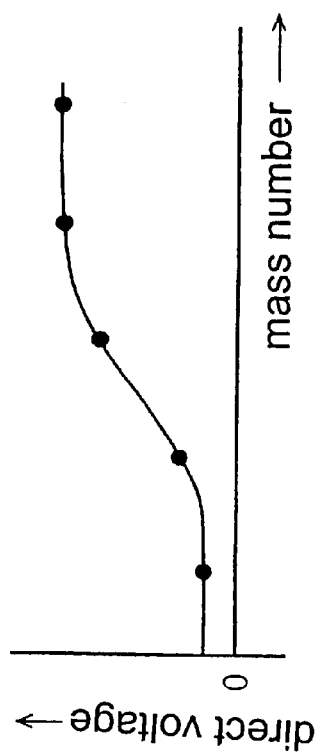
FIG. 3(a) and FIG. 3(b) are examples of voltage scanning patterns in the example of the LC/MS of the present invention.
Figure 3B:
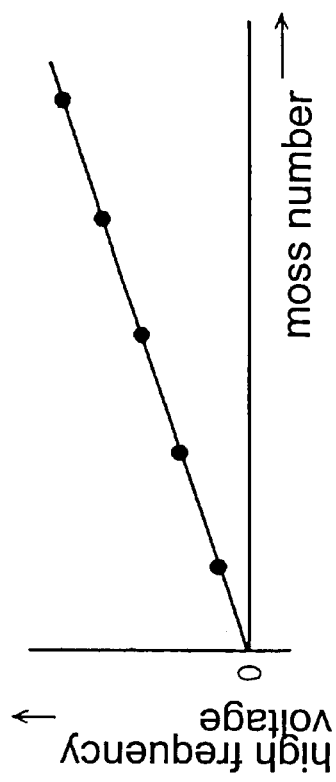

The voltage scanning pattern for the designated mass number range is experimentally known to have shapes as shown in FIG. 3(a) and FIG. 3(b) with respect to the direct current and the high frequency voltage, respectively. When the plural pairs of data for the mass number and the voltage (black circles in FIG. 3) are provided, the control portion 50 makes the voltage scanning pattern including the designated strait lines and the curve lines according to a designated algorithm. As a result, for example, the patterns are obtained as shown in FIG. 3(a) and FIG. 3(b). When the voltage scanning patterns corresponding to the direct current voltage and the high frequency voltage are made, they are stored as the voltage data to the mass numbers in the memory portion 51, respectively.

When the scanning measurement begins through the designated range, the control portion 50 controls the quadrupole voltage source 52 according to a range of mass numbers, a scanning speed or the like, and scans the impressed voltage with respect to the quadrupole filter 16. The voltage data corresponding to the mass number, which are previously stored in the memory portion 51, are read and sent to the voltage sources, synchronizing with the scanning. Accordingly, the applied voltages with respect to the solvent removing tube 18, the first ion lens 19 and the second ion lens 20 are scanned, respectively, synchronizing with the scanning of the applied voltage with respect to the quadrupole filter 16.

When the voltages are scanned, ions, each having an objective mass number, in the ions generated from the droplet which is atomized from the nozzle 15 pass through the solvent removing tube 18 very effectively. Furthermore, the ions having an objective mass number in the ions which are introduced into the first ion lens 19 through the solvent removing tube 18 are focused at the orifice of the skimmer 21 very effectively, and introduced into the second intermediate chamber 13. The ions having the objective mass number in the ions which are also introduced into the second ion lens 20 through the orifice of the skimmer 21 are focused at the pin hole 21 very effectively, and introduced into the mass spectrometry chamber 14. That is, the ions which have the specific mass number and are allowed to pass through the quadrupole filter 16 may only pass from the solvent removing tube 18 to the entrance of the quadrupole filter 16 at the best efficiency. A passing efficiency for other ions is lower than that of the ions with the specific mass number.

While the invention has been explained with reference to the specific embodiment of the invention, the explanation is illustrative and the invention is limited only by the appended claims.

What is claimed is:

1. A liquid chromatograph mass spectrometer, comprising:

a liquid chromatograph portion, an interface having an ionization chamber for atomizing at about an atmospheric pressure a liquid sample supplied from the liquid chromatography portion to ionize, and first and second intermediate chambers for passing an ionized sample therethrough with an ion optical axis, a mass spectrometry chamber having a mass separator in a vacuum condition, the ionized sample being introduced into the mass separator through the first and the second intermediate chambers, a solvent removing tube disposed in the interface for carrying a droplet including ions from the ionization chamber to the first intermediate chamber, a first ion lens disposed in the first intermediate chamber and having a plurality of board electrodes arranged along the ion optical axis, a second ion lens disposed in the second intermediate chamber and having rod electrodes with a number of 2n arranged along the ion optical axis, wherein n is an integer and at least two, a first voltage generation device attached to the solvent removing tube for applying direct current voltage thereto, a second voltage generation device connected to the board electrodes for applying high frequency voltage superposed on direct current voltage to the board electrodes, a third voltage generation device connected to the rod electrodes for applying high frequency voltage superposed on direct current voltage to the rod electrodes, a memory portion for storing voltage data corresponding to each mass number for the solvent removing tube, the first ion lens and the second ion lens to improve ion passage efficiency, and a control, device electrically connected to the first, second and third voltage generation devices for providing voltages to the first, the second and the third voltage generation devices based on data retained in the memory portion in applying appropriate voltages to the mass separator according to a mass number of an object to be analyzed.

2. A liquid chromatograph mass spectrometer according to claim 1, wherein the ion optical axis links between an exit of the solvent removing tube and an entrance pin hole of the mass spectrometry chamber.

3. A liquid chromatograph mass spectrometer according to claim 1, wherein said control device includes a pattern making portion for making a voltage scanning pattern.

4. A liquid chromatograph mass spectrometer according to claim 1, wherein the board electrodes are disk-shaped metal boards which are arranged at predetermined intervals along the ion optical axis, and which become closer to the ion optical axis in approaching an entrance pin hole of the mass spectrometry chamber.

5. A liquid chromatograph mass spectrometer according to claim 1, wherein the rod electrodes are disposed around the ion optical axis, touching internally a designated circle.

6. A liquid chromatograph mass spectrometer according to claim 1, further comprising quadrupole filter disposed in the mass spectrometry chamber.

* * * * *